US 6,968,235 B2
United States Patent
Belden et al.
(10) Patent No.: US 6,968,235 B2
(45) Date of Patent: Nov. 22, 2005

(54) ENHANCED METHOD AND APPARATUS TO IDENTIFY AND CONNECT A SMALL DIAMETER LEAD WITH A LOW PROFILE LEAD CONNECTOR

(75) Inventors: Elisabeth L. Belden, Maple Grove, MN (US); Eric V. Blaha, Hudson, WI (US); Eric H. Bonde, Victoria, MN (US); Ryan Cobian, New Brighton, MN (US); Steven D. Goedeke, Forest Lake, MN (US); Gregory J. Haubrich, Champlin, MN (US); Douglas N. Hess, Maple Grove, MN (US); Nels D. Nerison, Wyoming, MN (US); John L. Sommer, Coon Rapids, MN (US); David L. Thompson, Andover, MN (US); Jonathan C. Werder, Corcoran, MN (US)

(73) Assignee: Medtronic, Inc., Minneapolis, MN (US)

( * ) Notice: Subject to any disclaimer, the term of this patent is extended or adjusted under 35 U.S.C. 154(b) by 471 days.

(21) Appl. No.: 10/137,158

(22) Filed: Apr. 30, 2002

(65) Prior Publication Data
US 2003/0018364 A1 Jan. 23, 2003

Related U.S. Application Data (63) Continuation-in-part of application No. 09/907,308, filed on Jul. 17, 2001, now Pat. No. 6,675,049.

(51) Int. Cl.⁷ .................................................. A61N 1/34
(52) U.S. Cl. ......................................................... 607/60
(58) Field of Search ............................ 607/1, 30, 60, 607/61, 70, 115; 439/668; 128/899

(56) References Cited

U.S. PATENT DOCUMENTS

| 3,348,548 | A |   | 10/1967 | Chardack |
| 3,754,555 | A |   | 8/1973  | Schmitt |
| 3,814,104 | A |   | 6/1974  | Irnich et al. |
| 3,844,292 | A |   | 10/1974 | Bolduc |
| 3,974,834 | A |   | 8/1976  | Kane |
| 4,374,382 | A |   | 2/1983  | Markowitz |
| 4,485,813 | A |   | 12/1984 | Anderson et al. |
| 4,556,063 | A |   | 12/1985 | Thompson et al. |
| 4,583,543 | A | * | 4/1986  | Peers-Trevarton ............. 607/1 |
| 4,628,934 | A |   | 12/1986 | Pohndorf et al. |
| 4,730,188 | A |   | 3/1988  | Milheiser |
| 4,821,723 | A |   | 4/1989  | Baker, Jr. et al. |
| 5,025,550 | A |   | 6/1991  | Zirbes et al. |
| 5,041,826 | A |   | 8/1991  | Milheiser |
| 5,052,388 | A |   | 10/1991 | Sivula et al. |
| 5,127,404 | A |   | 7/1992  | Wyborny et al. |

(Continued)

Primary Examiner—George Manuel
(74) Attorney, Agent, or Firm—Girma Wolde-Michael; Michael C. Soldner (57) ABSTRACT

The present invention provides a practical, multi-polar, in-line connector system for use in connecting implantable medical devices (IMD) and associated non-standard, low profile medical electrical leads. In addition, the present invention provides a system that uses tool less, frictional, sealed, compressive electrical connections for most or all of the electrical interconnections between an IMD and a low profile lead. A protective sleeve seals the lead connector to the non-standard port to prevent intrusion of body fluids therein. In addition, optional microchip-based circuitry coupled to the sleeve enables wireless communication and remote programming for diverse IMDs. Memory associated with the circuitry can store, update and reprogram a wide variety of information relevant to the IMD, the patient, and the attending physician, among others. For example, the microchip may be used to identify the lead type and characteristics, as well as other useful data.

16 Claims, 8 Drawing Sheets

U.S. PATENT DOCUMENTS

| | | |
|---|---|---|
| 5,131,388 A | 7/1992 | Pless et al. |
| 5,144,524 A | 9/1992 | Tullis et al. |
| 5,144,949 A | 9/1992 | Olson |
| 5,154,170 A | 10/1992 | Bennett et al. |
| 5,158,078 A | 10/1992 | Bennett et al. |
| 5,166,676 A | 11/1992 | Milheiser |
| 5,199,428 A | 4/1993 | Obel et al. |
| 5,207,218 A | 5/1993 | Carpentier et al. |
| 5,246,014 A | 9/1993 | Williams et al. |
| 5,252,962 A | 10/1993 | Urbas et al. |
| 5,271,395 A | 12/1993 | Wahlstrand et al. |
| 5,281,855 A | 1/1994 | Hadden et al. |
| 5,300,120 A | 4/1994 | Knapp et al. |
| 5,312,453 A | 5/1994 | Shelton et al. |
| 5,314,430 A | 5/1994 | Bardy |
| 5,330,507 A | 7/1994 | Schwartz |
| 5,331,966 A | 7/1994 | Bennett et al. |
| 5,354,316 A | 10/1994 | Keimel |
| 5,374,279 A | 12/1994 | Duffin, Jr. et al. |
| 5,397,343 A | 3/1995 | Smits |
| 5,423,334 A | 6/1995 | Jordan |
| 5,534,018 A | 7/1996 | Wahlstrand et al. |
| 5,545,186 A | 8/1996 | Olson et al. |
| 5,546,698 A | 8/1996 | Rock |
| 5,626,630 A | 5/1997 | Markowitz et al. |
| 5,782,891 A | 7/1998 | Hassler et al. |
| 5,824,030 A | 10/1998 | Yang et al. |
| 5,833,603 A | 11/1998 | Kovacs et al. |
| 5,843,141 A | 12/1998 | Bischoff et al. |
| 5,919,221 A | 7/1999 | Miesel |
| 6,016,447 A | 1/2000 | Juran et al. |
| 6,044,302 A | 3/2000 | Persuitti et al. |
| 6,085,118 A | 7/2000 | Hirschberg et al. |
| 6,178,355 B1 | 1/2001 | Williams et al. |
| 6,409,674 B1 | 6/2002 | Brockway et al. |
| 6,755,694 B2 * | 6/2004 | Ries et al. .................. 439/668 |

* cited by examiner

ENHANCED METHOD AND APPARATUS TO IDENTIFY AND CONNECT A SMALL DIAMETER LEAD WITH A LOW PROFILE LEAD CONNECTOR

CROSS-REFERENCE TO RELATED APPLICATIONS

This Application is a continuation-in-part of U.S. patent application Ser. No. 09/907,308, filed Jul. 17, 2001, now U.S. Pat. No. 6,675,049 entitled "Method and Apparatus for Automatic Implantable Medical Lead Recogniton and Configuration," which is incorporated herein by reference in their entirety.

FIELD OF THE INVENTION

The present invention relates generally to mechanisms for interconnecting electrical leads to an implantable medical device (IMDs), and more particularly, to the connection of a non-standard, low profile (small diameter) lead to an IMD. Even more specifically, the present invention relates to the connecting and identifying a small diameter lead within a low profile lead port located in the connector block, or header, assembly of an IMD.

BACKGROUND OF THE INVENTION

As implantable electrical devices have increased in their complexity, there have been an increasing variety of lead systems developed for use in conjunction with these devices. Nowhere is this more apparent than in the context of implantable cardioverter/defibrillators and biventricular IMDs to treat congestive heart failure. These IMDs require the use of three or more leads. The leads themselves may carry one, two, three (or more) electrodes, and may employ a variety of different electrical connector configurations and types. As a result, manufacturers of such devices have had to produce their products with a variety of connector block configurations, capable of use with different lead systems. For example, Medtronic, Inc. presently manufactures implantable cardioverter/defibrillators with four basic connector designs, designated configurations "B," "C," "D," and "E." The "B" configuration includes three 6.5 mm connector ports for receiving high voltage electrical lead connectors of the type used to couple to cardioversion/defibrillator electrodes and one 3.2 mm in-line electrical connector port compatible with the IS-1 connector standard for receiving an IS-1 electrical lead connector of the type generally used to couple to cardiac pacing and sensing electrodes. The "C" configuration includes a single 3.2 mm connector bore conforming to the DF-1 standard for receiving high voltage electrical lead connectors for coupling to cardioversion/defibrillation electrodes. This configuration also includes a single IS-1 connector bore. The "D" configuration includes three DF-1 connector bores and one IS-1 connector bore. The "E" configuration includes two 6.5 mm connector bores and two 5 mm connector bores for receiving electrical lead connectors used to couple to individual cardiac pacing and sensing electrodes.

As is apparent from the above discussion, multiple connector block types are necessitated both by the use of multiple connector standards, and also because of the desire to connect a varying number of lead systems used for specific purposes to a given device. The situation is complicated even further by the use of non-standard connector systems. For example, it has been increasingly common to utilize small-diameter guide catheters to deliver leads having a diameter of 7 French or less to a desired implant site.

With the increased use of multi-chamber pacemakers and defibrillators such as those that provide bi-atrial or bi-ventricular pacing capabilities, multiple leads are required to deliver electrical stimulation to various locations within the heart. With the use of multiple leads that are positioned within one or more small vessels of the body, it has become even more important to minimize lead and lead connector size. As leads become smaller, it becomes increasingly difficult to connect these small diameter leads to and within the connector block of an IMD during an implant procedure. In addition, it also becomes increasingly difficult to mark these smaller diameter leads with the appropriate identification, including manufacturer identification and/or lead model and serial numbers.

The issue of marking and/or identifying small diameter lead has been addressed in several ways in the art. The following patents are exemplary of the plurality of approaches: U.S. Pat. No. 5,824,030 to Yang, U.S. Pat. No. 5,374,279 to Duffin, U.S. Pat. No. 4,628,934 to Pohndorf, U.S. Pat. No. 6,085,118 to Hirschberg, U.S. Pat. No. 5,300,120 to Knapp, U.S. Pat. No. 5,833,603 to Kovacs, U.S. Pat. No. 5,423,334 to Jordan and U.S. Pat. No. 5,252,962 to Urbas. While the above publications teach various improvements to the art, they do not address the problems of identifying small diameter leads or of coupling non-standard, small diameter leads to header module of an IMD.

SUMMARY OF THE PRESENT INVENTION

The present invention provides a practical, multi-polar, in-line connector system for use in connecting IMDs and their associated leads. In addition, the present invention provides a system that uses tool less, frictional, sealed compressive electrical connections for most or all of the electrical interconnections between the IMD and a low profile lead. The present invention also provides a manually positionable protective sleeve member that seals the connector to the port to prevent intrusion of body fluids into the lead connector block. The protective sleeve also prevents abrasion of the lead's insulation at the lead's proximal distal end where it joins to the connector block. The protective sleeve is a separate component which is placed into position after an introducing structure, such as a catheter, has been removed from the lead body of a lead after the lead is appropriately situated by a physician. Because the lead and connector are very compact, the catheter may be simply pulled over the connector with cutting, or slitting, the catheter. The protective sleeve may be positioned on the lead either before or after the connector is coupled to the connector block. In the former case, a sleeve member having a bore with an inner diameter approximately the same size as the corresponding portion of the lead is simply impaled on the proximal end of the lead. In the latter case, a sleeve member having an axial slit is pressed into engagement with the lead so that a segment of the lead passes through the slit.

In addition, in one form of the present invention a microchip is embedded into the protective sleeve that may provide wireless communication with external devices. The microchip can store information, update such information, program and reprogram the microchip, among others. For example, the microchip may be used to identify the lead type and characteristics, as well as other useful data that may be downloaded to the microchip. These include the date of implant, measured stimulation and sensing threshold data, among others.

The present invention provides these benefits by taking a substantially different approach to the insertion of the lead into the connector block. This mechanism uses a pull tool connected to the lead connector pin to pull the lead into the connector block bore. This method is disclosed in U.S. Pat. No. 5,843,141 issued to Bischoff et al., and incorporated herein by reference in its entirety. The connector block may correspond to any of the connector blocks proposed for multipolar, in-line connectors commonly used by those familiar with the art. An axial bore is provided which receives the pull tool in alignment with the rear of the non-standard port. The connector port (and axial bore for the pull tool) define openings on opposing sides of the connector block. After the pull tool seats the lead in the connector port both openings are sealed. The connector port is sealed with respect to the medical lead and the axial bore for the pull tool is sealed using conventional means. That is, the axial bore may be plugged with a grommet or cover and adhered in place. Alternatively, the cover for the axial bore may be ultrasonically welded to the surrounding surface of the header module. In the case of a grommet formed of silicone or other pliable self-sealing material, after the pull tool is retracted from the axial bore, the grommet returns to a sealed state. The pulling tool is provided with a rod that carries a connection mechanism, such as a threaded extension to engage with the proximal end of the lead assembly.

The pulling tool has an enlarged head, knob-type feature, on its proximal end to assist a user in manually engaging (e.g., screwing) the distal end of the tool to the proximal end of the lead pin to enable pulling the lead into the connector block. To promote ease of connection between the pull tool and the lead pin of the lead assembly, the pull tool is sufficiently long that the distal end of the pull tool extends outside of the port and can be readily and easily manually connected in plain view. Thus, the physician can easily see how to mate the pulling tool with the connector pin. When mated, the pulling tool is used to pull the lead fully into the connector block. When fully seated in position in the port, the lead and block conductors are aligned with one another and thus establish electrical communication. An internal stop surface within the connector block and a visual indicator on the pulling tool may be used to assist in proper alignment and/or to confirm that the lead is fully seated. Of course, the pulling tool is uncoupled from the lead and the connector block prior to implantation of the IMD.

The connector block of the IMD has electrical connections that frictionally engage the electrode(s) on the low profile lead, rather than using the traditional set screw type connectors. This type of connector assembly is usually adequate to retain the lead within the connector block. However, optionally, a single set screw type connector or other additional mechanical locking mechanism may be used as well, if only to alleviate any concern regarding the security of the coupling.

The present invention provides a mechanism to automatically identify one or more leads that may be associated with the IMD. In another form of the present invention, an radio frequency (RF) communication chip that is attached to, or integrated within, the low profile lead or the protective sleeve. The RF chip may store data such as model and serial numbers, technical information, and calibration data, among others. At the time of implant or sometime thereafter, this information may be communicated to a programmer or other device such as a personal data management (PDM) unit, a Personal Digital Assistant (PDA), or the like and stored, processed and the like. The data is inherently susceptible of being transmitted via wired or wireless networks to remote facilities. The data may include the presence of the lead, date of implantation, manufacturer, version number, and myriad other coded information, as well as simply to identify the type of lead. The data can be used, for example, to automatically adjust amplifier gains or other circuitry associated with the lead. These data may be entered into a patient record on an external programmer or transferred to a central storage location for use by health care providers when performing diagnoses and prescribing therapies associated with the IMD. Optionally, the RF communication circuit or microchip may be formed on a flexible substrate and wrapped around a portion of the lead (e.g., disposed underneath or within the protective sleeve).

BRIEF DESCRIPTIONS OF THE DRAWINGS

FIGS. 6A, 6B, and 6C are is elevational views in cross section depicting three embodiments of a non standard port and the resulting curvature of a low profile lead inserted therein and wherein FIG. 6A and FIG. 6C depict non-standard ports each with a strain relief zone while FIG. 6B depicts a non-standard port without a strain relief zone.

DETAILED DESCRIPTION OF THE ILLUSTRATED EMBODIMENTS

Figure 1:
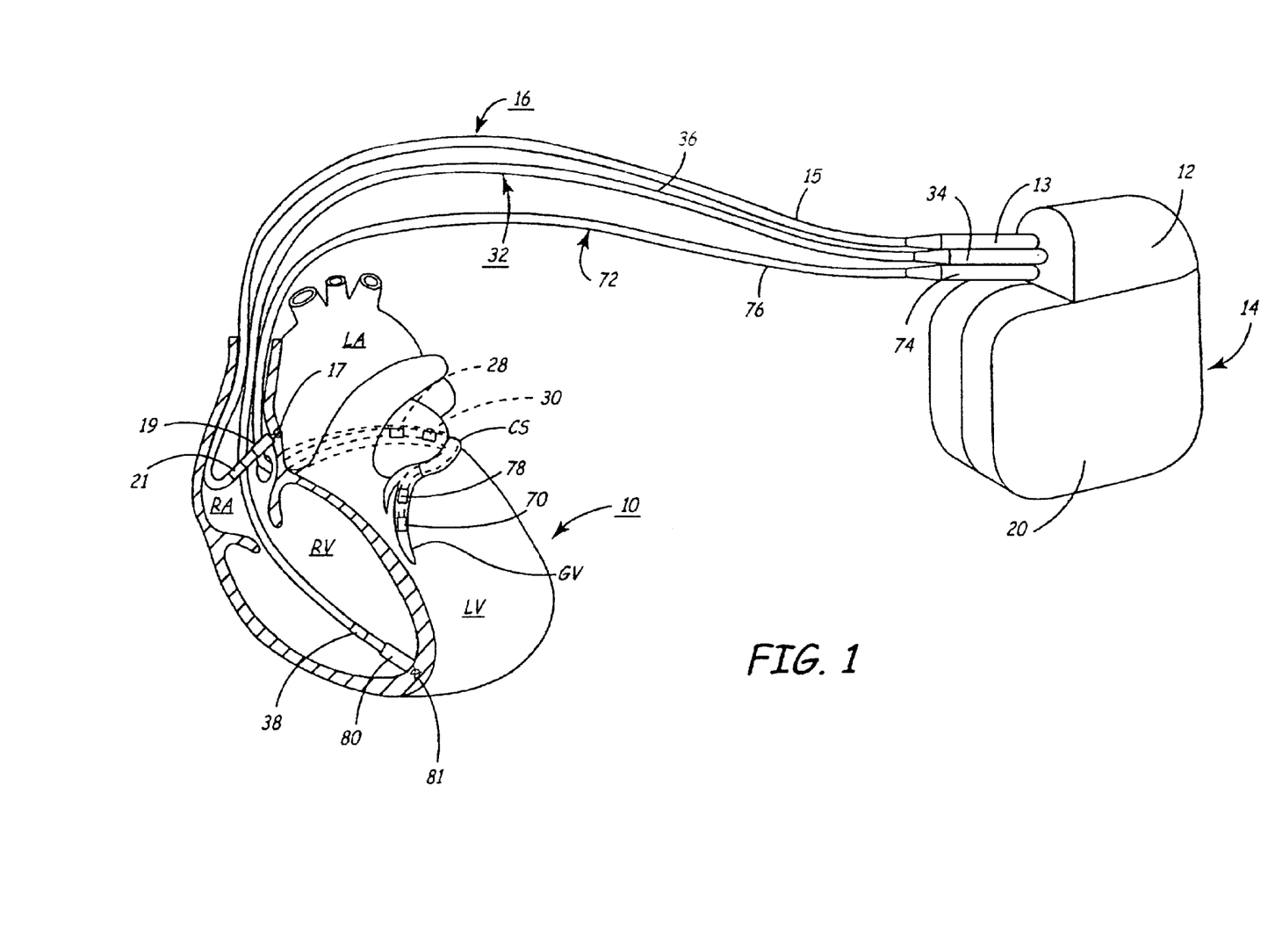
FIG. 1 is a schematic representation of an implanted three channel IMD and associated leads in which the invention is practiced.

FIG. 1 is a schematic representation of an implanted, three channel IMD typically used to treat congestive heart failure (CHF). IMD 14 is implanted subcutaneously in a patient's body between the skin and the ribs. Three endocardial leads 16, 32 and 72 connect IMD 14 to right atrium (RA), right ventricle (RV) and left ventricle (LV), respectively, through connector block 12. Any one or more of leads 16, 32, and 72 may be a low profile lead that embodies the characteristics of the present invention, hereinafter described. A remote indifferent electrode may be formed as part of the outer surface of housing 20 of IMD 14 for unipolar pacing.

The present invention will be described herein as an IMD used to provide therapy for CHF. Those of ordinary skill in the art, however, with the benefit of the present disclosure will appreciate that the present invention may be advantageously practiced in connection with numerous other types of IMDs such as defibrillators, cardioverters, and the like. Indeed, the present invention may be practiced in any application in which it is desirable to provide an electrical connection for sensing cardiac or other corporeal signals and delivering electrical signals to the heart or other corporeal tissue.

The depicted bipolar endocardial RA lead 16 is passed through a vein into the RA, and the distal end of RA lead 16 is implanted in the RA appendage or fixed to the RA wall by a positive fixation mechanism 17. Bipolar endocardial RA lead 16 is connected via a connector 13 fitting into connector block 12 that is coupled to a pair of electrically insulated conductors within lead body 15 and connected to distal tip RA pace/sense electrode 19 and proximal ring RA pace/sense electrode 21. Delivery of atrial pace pulses and sensing of atrial depolarizations occurs between the distal tip RA pace/sense electrode 19 and proximal ring RA pace/sense electrode 21, wherein the proximal ring RA pace/sense electrode 21 functions as an indifferent electrode. Alternatively, a unipolar endocardial RA lead could be substituted for the depicted bipolar endocardial RA lead 16 and be employed with indifferent housing electrode 20. Bipolar, endocardial RV lead 32 is passed through a vein and the RA chamber of heart 10 and into the RV where its distal ring and tip RV pace/sense electrodes 38 and 80 may be fixed in place in the RV apex by a conventional distal attachment mechanism 81. The RV lead 32 is fitted via a connector 34 into a bipolar bore of connector block 12 that is coupled to a pair of electrically insulated conductors within lead body 36 and connected with distal tip RV pace/sense electrode 80 and proximal ring RV pace/sense electrode 38.

In this illustrated embodiment, a bipolar, endocardial coronary sinus (CS) lead 72 is passed through a vein and the RA chamber of the heart 10 into the CS and then inferiorly into a branching vessel of the great vein (GV) to extend the proximal and distal LV CS pace/sense electrodes 78 and 70 alongside the LV chamber. The distal end of such a CS lead is advanced through the superior vena cava, the right atrium, the ostium of the coronary sinus, the coronary sinus (CS), and into a left descending coronary vein, such as the GV.

In a four chamber/channel embodiment, LV CS lead 72 could bear proximal LA CS pace/sense electrodes 28 and 30 positioned along the CS lead body to lie in the larger diameter CS adjacent the LA. Typically, LV CS leads and LA CS leads do not employ any fixation mechanism and instead rely on the close confinement within these vessels to maintain the pace/sense electrode or electrodes at a desired site. The LV CS lead 72 is formed with a multiple conductor lead body 76 coupled at the proximal end connector 74 fitting into a bore of connector block 12. A small diameter lead body 76 such as one disclosed in the present invention is selected in order to lodge the distal LV CS pace/sense electrode 70 deeply in a vein branching inferiorly from the great vein GV.

In this case, the CS lead body 76 would encase four electrically insulated lead conductors extending proximally from the more proximal LA CS pace/sense electrode(s) and terminating In a dual bipolar connector 74. The LV CS lead body would be smaller between the LA CS pace/sense electrodes 28 and 30 and the LV CS pace/sense electrodes 78 and 70.

Figure 2:
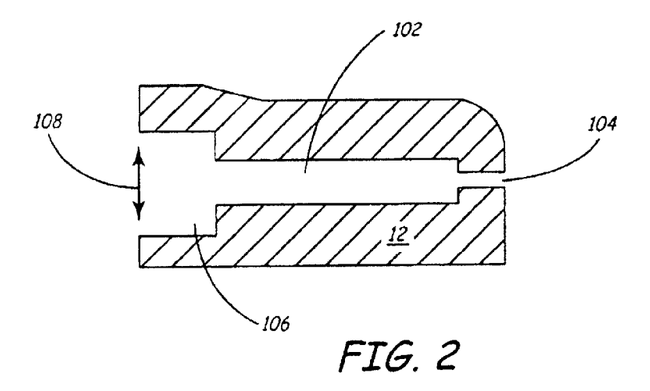
FIG. 2 is an elevational view in cross section of a low profile in-line connector block assembly with both a proximal and distal opening.

FIG. 2 is an elevational view in cross section of that portion of connector block 12 with one port 102 of the three in FIG. 1 that is specifically designed and built to accommodate relatively "small" diameter in-line lead 76. The "small" diameter lead may be ≦5F. One or two other ports in connector block 12 are standard ports designed to accommodate an IS-1 or DF-1 lead. CS lead 76 used to pace/sense the left side of the heart for CHF has a low profile, non-standard connector that is connected to the device within the non-standard port 102. Port 102 extends freely from the proximal to the distal opening and contains seals and contact zones (not shown) as are disclosed in U.S. Pat. No. 5,843,141. Pull tool entry zone 104 contains a self-sealing material (not shown), composed of one of a plurality of materials known to those familiar with the art. Pull tool entry zone is of such a diameter that easily accommodates the lead tool (see FIG. 3). Strain relief zone 106 is designed to have a depth and width to accept an enlarged flexible sleeve or collar that provides strain relief and additional protection for the portion of the lead body positioned adjacent to the connector module.

Figure 3A:
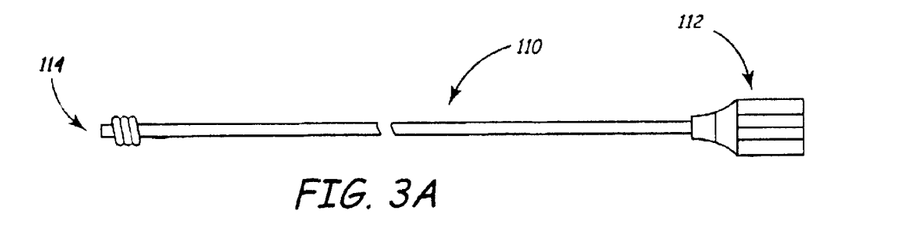
FIG. 3A is a schematic diagram of the pulling tool used to connect to the lead and pull the lead into the low profile bore of the connector block.

FIG. 3A illustrates pulling tool 110, equipped with knob 112 to facilitate the user's effort to pull the attached lead into the low profile bore of the connector block. Distal end 114 may consist of a threaded design to engage the lead, although other designs may be used to couple the lead including, among others, a spring loaded clip or a plug to form a pressure fit with the opening in the lead's connector pin.

Figure 3B:
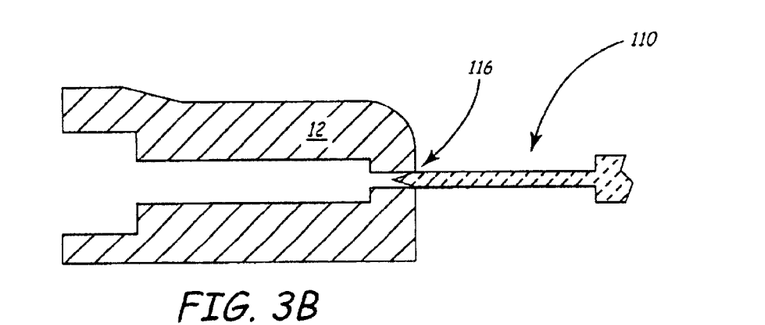
FIG. 3B is an elevational view in cross section of the connector block assembly showing the partial insertion of the pulling tool into the low profile bore of the connector block.
Figure 3C:
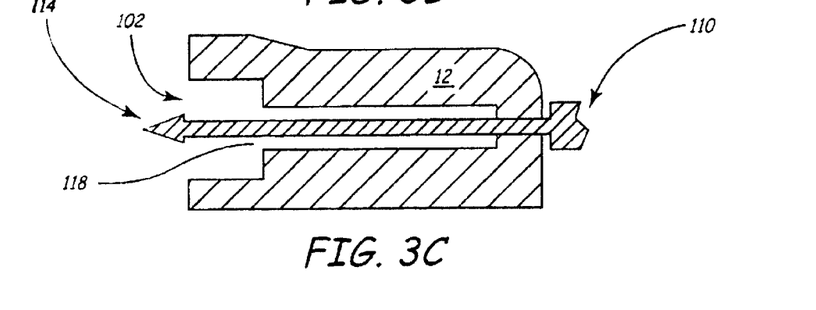
FIG. 3C is an elevational view in cross section of the connector block assembly showing the full insertion of the pulling tool into the low profile bore of the connector block.

In FIGS. 3B and 3C, the pull tool 110 is shown at the start of insertion in FIG. 3B and fully inserted 113 in FIG. 3C. Lead pull tool 110 is inserted into axial bore 116 until the distal end 114 of the pull tool 110 extends outside the port 102 of connector module 12 as shown in FIG. 3C. The distal end 114 of pull tool 110 preferably protrudes at least beyond strain relief zone 118 of port 102 during coupling of pull tool 110 to the lead. The pull tool is also preferably pre-loaded (i.e., partially assembled) into the port 102 during the manufacturing process as depicted in FIG. 3C. When lead pull tool 110 is pre-loaded, the port is effectively occluded to prevent the insertion of other with connectors that are not designed to connect with the lead pull tool 110. In any event, the pull tool 110 can be color-coded or have a small symbol or other visual indication to further distinguish the non-standard port 102. On the other hand, the lead pull tool may be separately packaged so that the physician has the responsibility of inserting pull tool 110 as shown in FIG. 3B.

When the pull tool is pre-loaded embodiment both ends of the lead pull tool preferably extend outside the connector bore (i.e., the port 102 and axial bore 104). Thus, the lead pull tool 110 protrudes from the non-standard port 102 and thus provides a visual indication that the port 102 is non-standard, thereby minimizing inadvertent insertion of a standard lead therein. A lead designed for mating with the lead pull tool 110 can be mated outside the connector bore. The physician has an enhanced ability to perform this attachment since both the distal end 114 of the lead pull tool 110 and the proximal end of the lead are readily available for visual identification and manipulation.

Figure 4A:
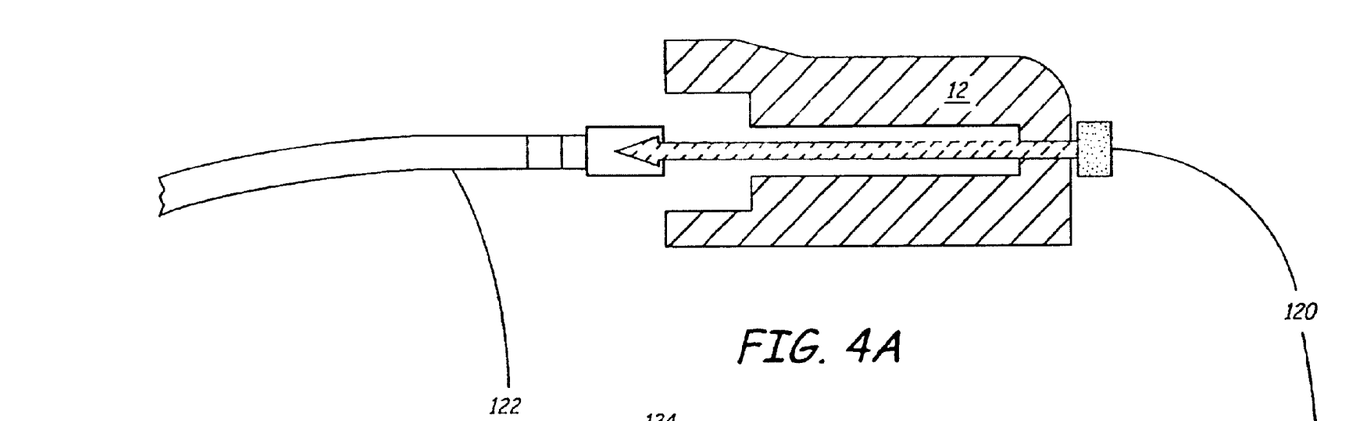
FIG. 4A is an elevational view in cross section illustrating the pull tool mated to the low profile lead outside the connector block, with the lead within a delivery catheter.
Figure 4B:
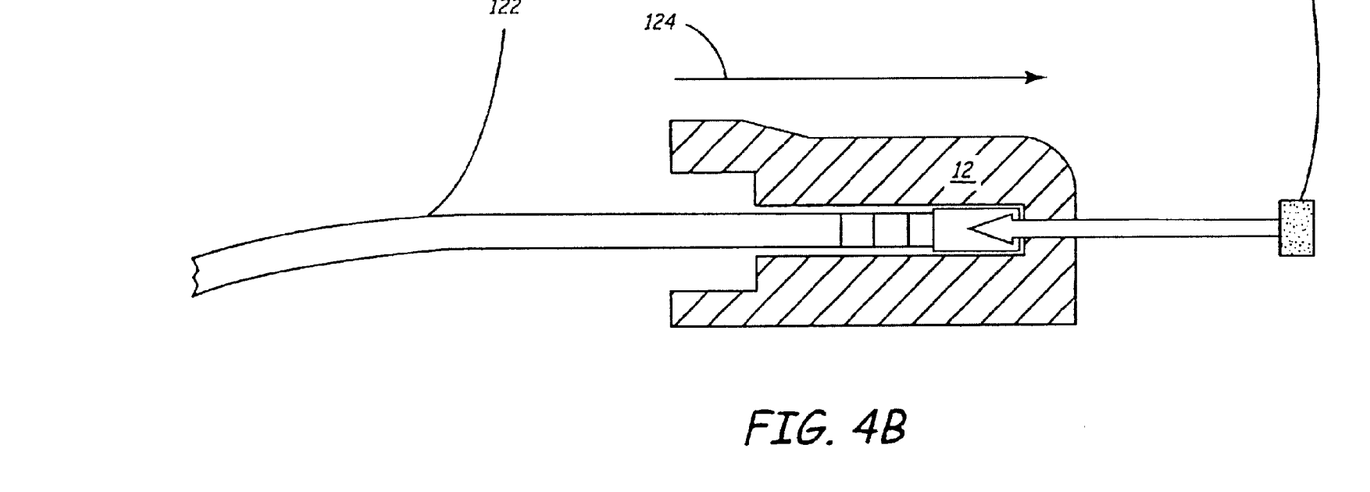
FIG. 4B is an elevational view in cross section showing the low profile lead fully drawn into a non standard, low profile port of the connector block.

FIG. 4A displays lead 122 coupled to the distal end of pull tool 120. While not depicted, an introducer catheter is used to deliver low profile lead through the left coronary veins of the left heart (see FIG. 1). Then, because the outer diameter of the connector and lead body of the low profile lead 122 is usually smaller than the inner diameter of the catheter, the catheter is simply pulled over the lead. The protective sleeve may be coupled to the lead 122 at this time (with a unitary, non-perforated sleeve). Thus, another advantage of the present invention is that no manual cutting (or slitting) of the catheter is required. Then, the distal end of lead pull tool 120 is preferably extended outside of the non-standard port to so that visual inspection and ease of connection to the lead 122. After the pull tool 120 is mated to the proximal end of low profile lead 122 the pull tool 120 is retracted thus urging the lead 122 into the low profile bore of the connector block 12. In an alternative embodiment, the protective sleeve may be coupled to the lead 122 after the pull tool is connected to the lead 122 (or even after the lead 122 has been retracted into the connector block 12). In this embodiment, a protective sleeve having a slit may be used (e.g., see FIG. 5). A portion of lead 122 is simply introduced into the slit, the protective sleeve compressed slightly (if required) and an end portion of the sleeve is inserted into the strain relief zone of the connector block 12.

Upon completion of mating of pull tool and lead 122 in FIG. 4A, the physician pulls proximal end of lead 122 fully into bore of connector block 12 (in direction indicated by arrow 124). With low profile lead 122 fully in place within port 102, the physician disengages and detaches lead pull tool 120 from low profile lead 122 by any one of a plurality of mechanisms, reverse rotation, collapsing the distal attaching end, among others.

Figure 5:
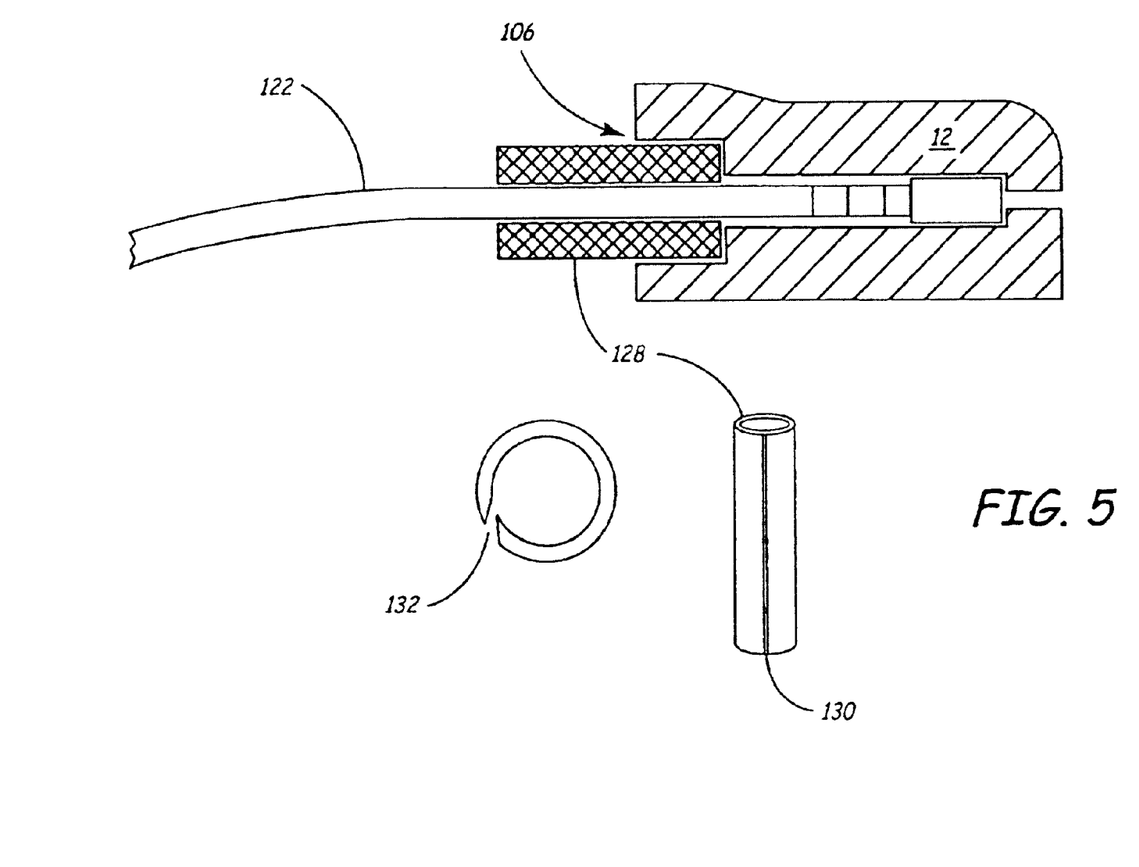
FIG. 5 is a three part illustration in which the first part is an elevational view in cross section showing a protective sleeve assembled into a non standard port to prevent stress and abrasion on/of the lead insulation, the second part is a plan view of an embodiment of a protective sleeve having a longitudinal slit and the third part is a perspective view of a protective sleeve having a longitudinal slit.

FIG. 5 shows the inclusion of protective sleeve 128 that is wrapped around low profile lead body 122 after insertion of its proximal end into strain relief zone 106. The design of protective sleeve 128 is such that it with manual application of pressure, the sleeve 128 frictionally fits within strain relief zone 106 with the result that the lead is held in place over the life of the implant. Protective sleeve 128 also provides additional sealing to prevent ingress of body fluids into the bore. As in the embodiment in FIG. 8, protective sleeve 128 may be fitted with a microchip. Protective sleeve 128 has longitudinal slit 130 that has overlapping design 132 that, when in place within strain relief zone 106, compresses the edges of protective sleeve 128 together. Such compression provides a seal to prevent intrusion of body fluids into the bore.

Without protective sleeve 128, the low profile lead connector has an increased likelihood of problems associated ingress of body fluids into port 102 and in general, with the region that interface with the IMD connector module 12. Such problems include: severe bending where the lead exits the connector module, abrasion of the lead body that is wrapped around or behind the IMD, the vulnerability of the lead's insulation to cuts and nicks at the time of IMD change out, and the illegibility of labeling on such a small-diameter lead. Protective sleeve 128 increases the radius of the bend that the lead body takes as it is wrapped around the device. Protective sleeve 128 also protects the lead's outer insulation from abrasion in the area where it could come into contact with the connector block. Protective sleeve 128 can optionally be manufactured to carry a programmable chip that could be programmed to carry lead information as is disclosed in the previously cited co-pending U.S. patent application (Ser. No. 09/907,308). Both the sleeve 128 and the interface of the sleeve with the major, strain relief zone opening 106 solves the problems that a small diameter lead body may encounter with bending and wrapping within the pocket containing the IMD and other lead(s) while, at the same time, preserving the advantages of a small diameter lead body. Such bending or wrapping of the lead around the body of the IMD is further discussed in U.S. Pat. No. 5,546,698 issued to Byland et al., and incorporated herein by reference in its entirety.

Figure 6A:
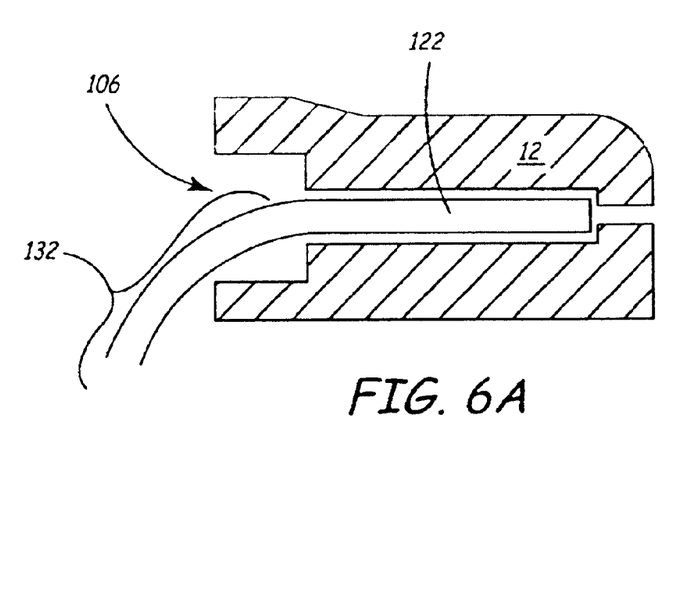
Figure 6B:
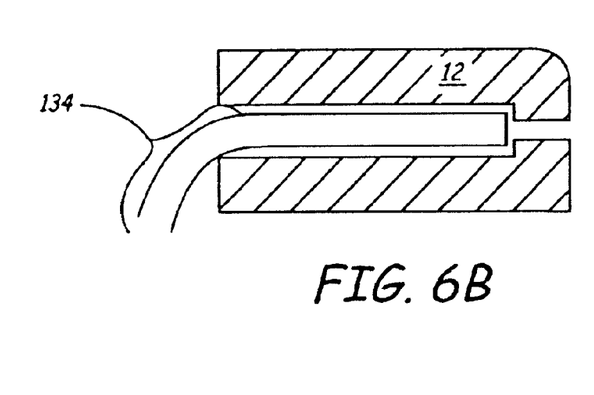
Figure 6C:
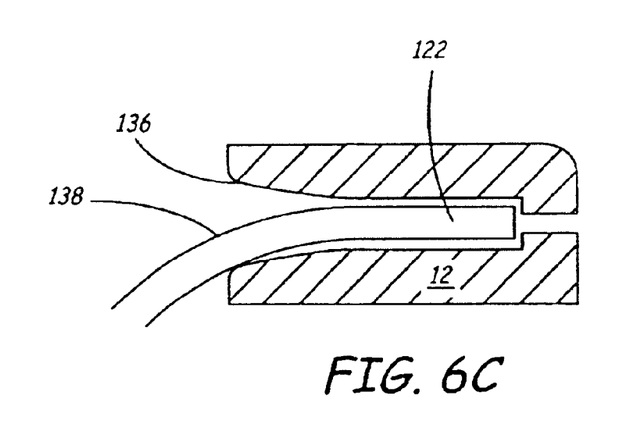

FIG. 6A depicts a low profile lead 122 fully inserted into a connector block 12 wherein the lead 122 is not equipped with a separate protective sleeve member. However, strain relief zone 106 provides partial support for lead and, thus, results in a less severe bending of lead at region 132 upon exiting from connector bore. In FIG. 6B, however, radius of lead is quite severe at region 134 due to the use of a connector without a strain relief zone. The partial support in FIG. 6A, however, would still subject the lead body to abrasion and nicking as mentioned above with respect to FIG. 5. An alternative to the preferred embodiment incorporating a strain relief zone is the embodiment depicted in FIG. 6C. This embodiment does not require a strain relief zone since the bore is fabricated with curved bevel 136 that results in a gentle bend 138 in lead 122. In this design, there is no need for a protective sleeve, as is found in the preferred embodiment. In this embodiment, the perimeter of the bevel 136 at the surface of header module 12 has a major radius resulting in smoothly rounded edges. While none of these three drawings depicts an appropriately shaped protective member, each embodiment depicted may utilize such a member. In the case of FIG. 6A the protective sleeve may be a resilient tube member approximately three to six inches (3"–6") in length with an inner lumen having a diameter of approximately 0.040" to 0.090" and an outer diameter of approximately 0.125" to 0.200" (so that a tight fitting connection is created when the sleeve is inserted into the strain relief zone) in accordance with the present invention. In the case of FIG. 6B, the protective sleeve can be a relatively thin, triangular member (in cross section) or a conical member with an axial bore to admit the body of the lead. In the alternative, a protective sleeve adapted for the structure depicted in FIG. 6B could be a sheet of resilient material or a thin tubular member. In the case of FIG. 6C, the protective sleeve can comprise a conical member with a bore or a cylindrical member which is pressed into the port until sufficient sleeve-retaining friction is generated. While not preferred, the protective sleeve members may be adhered into place.

Furthermore, while not depicted, the protective sleeve member(s) may have an arbitrary shape in which case the strain relief space of the non-standard port would preferably have a complementary shape. For example, in plan view, the strain relief space might appear triangular, square, oval, or other geometric shape. Such shape would provide added benefit to a physician in correctly connecting leads to a multi-port header module. In addition or in lieu of such physical "keying" of the non-standard port/lead coupling, the mating parts may be color-coded to increase accuracy to the process of connecting the leads to the header module. Furthermore, the protective sleeve can be formed of a material that is resistant to being inadvertently cut, as for example during a changeout procedure for an IMD. In this form of the invention, the protective sleeve has a layer of resilient material to protect the medical electrical lead.

Figure 7:
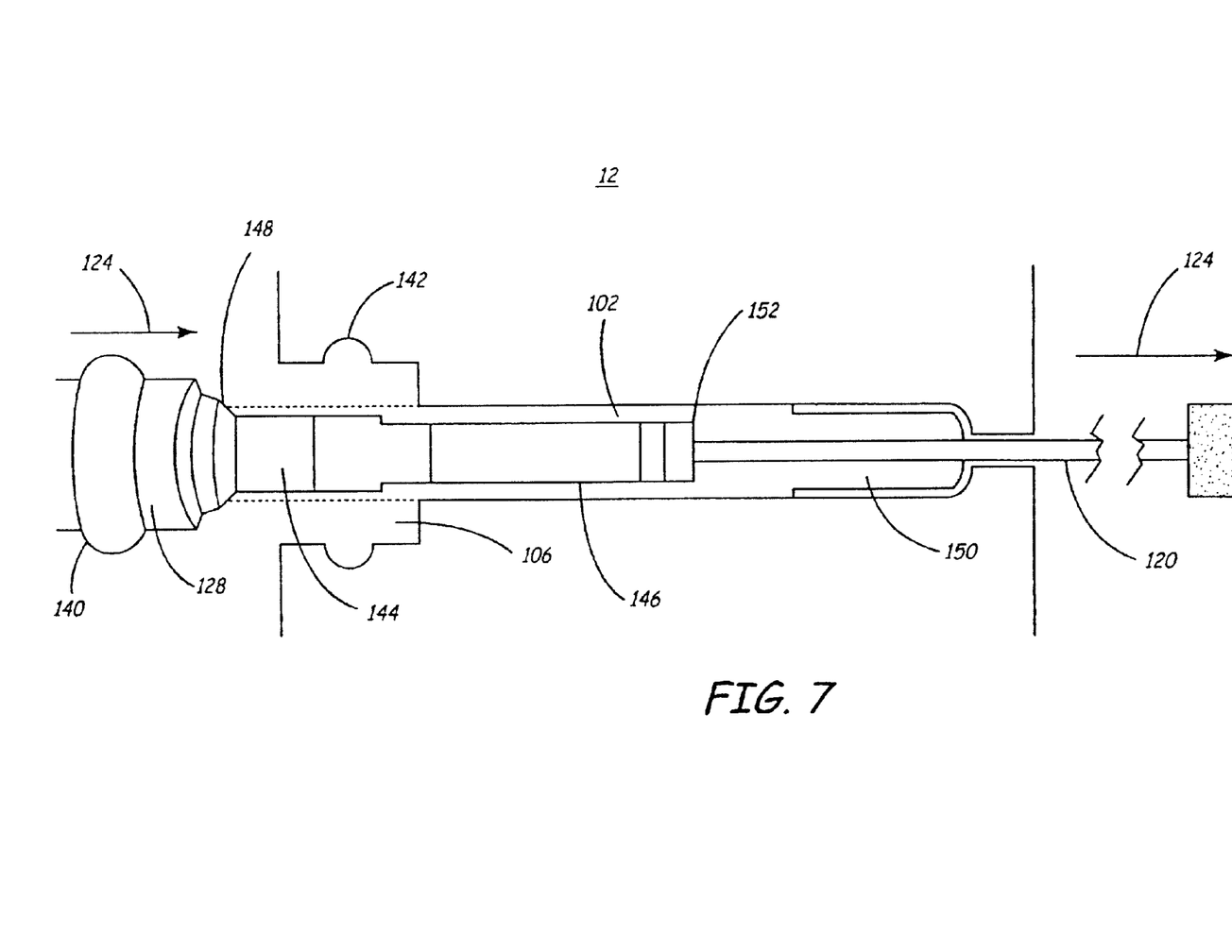
FIG. 7 is a partially exploded elevational view in cross section of a low profile lead, partially positioned within the lead bore of the connector block. The protective sleeve is equipped with an annular ring and abutting beveled surfaces designed to seal the port from the intrusion of body fluids.

FIG. 7 displays a blown-up illustration of connector port 12 during the process of using lead pull tool 120 to pull (in direction indicated by arrow 124) low profile lead into lead port 102. Lead pull tool 120 mates at 152 with lead tip 146. When fully seated in lead port 102, lead tip 146 will fit into proximal end 150 of lead port 120. Electrical contacts (not shown) are positioned within lead port 102 to provide electrical communication for lead tip 146 and ring 144 for pacing and sensing functions.

Protective sleeve 128 fits over lead body 148. When lead is pulled fully into lead port 102, ring 140 of protective sleeve 128, when mated into groove 142 within strain relief zone 106, serves to lock and seal the lead and ring 140 into place within lead port 102.

Figure 8:
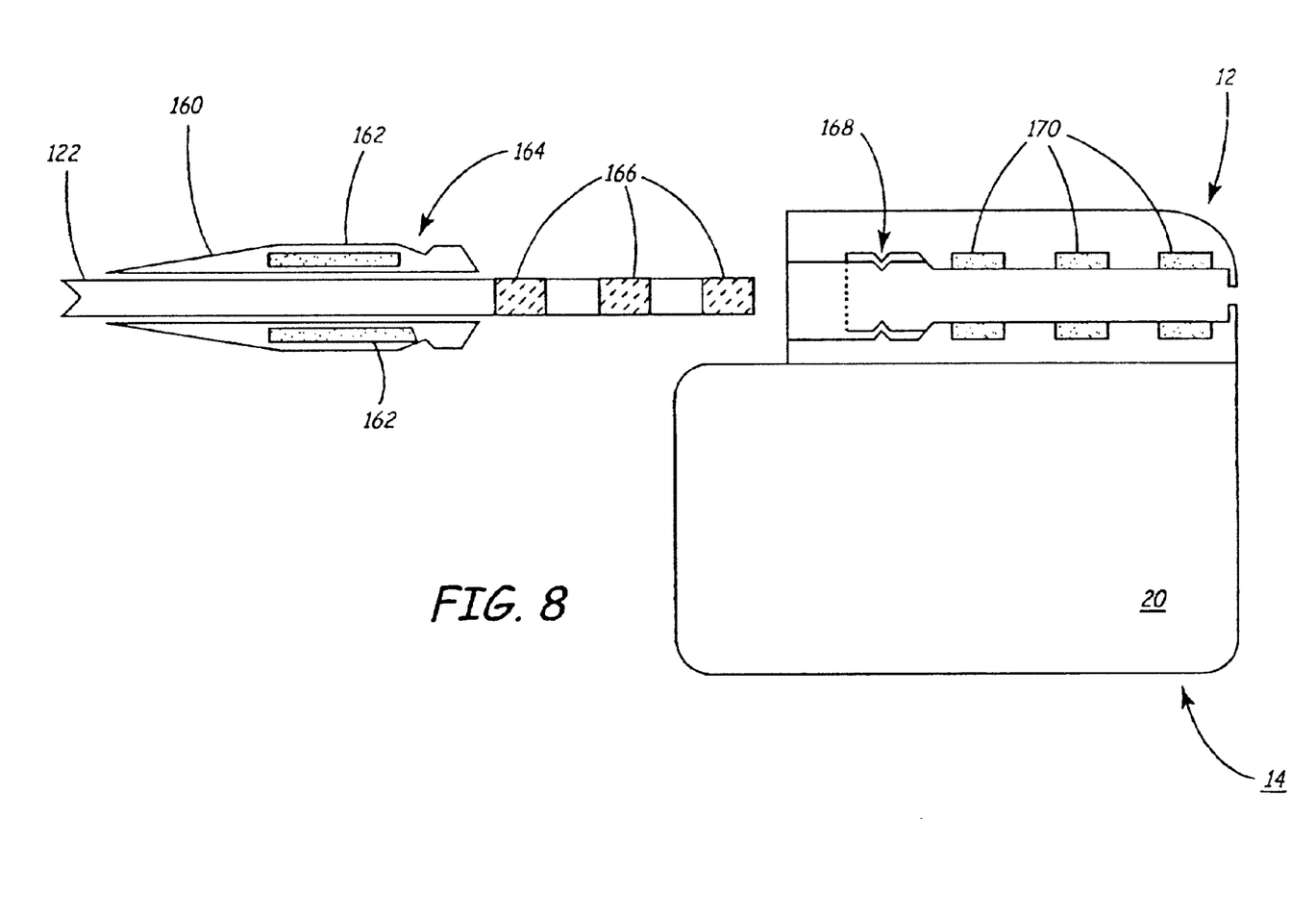
FIG. 8 is an elevational view in cross section of a low profile lead equipped with a programmable integrated circuit chip that may be programmed to transmit, receive, store and process data regarding the lead, the patient, the IMD, a variety of coded information and other pertinent data.

FIG. 8 shows one among a plurality of solutions to a method of providing the lead serial number and other information. One of the preferred embodiments of the present invention depicts lead 122 around which is protective sleeve 160 that can be of any length. Protective sleeve 160 has locking mechanism 164 that fits snugly into internal lock 168 of connector block 12. Alternatively, the seal may be part of the connector bore. Protective sleeve may, for example, correspond to protective sleeve depicted in FIG. 5.

Lead 122 may be equipped with one to three electrodes 166 that correspond to contacts 170. When lead 122 is fully deployed within connector block 12, electrical connection occurs between electrodes 166 and contacts 170, for purposes of sensing and pacing.

Microchip 162 preferably has communication circuitry, memory storage and processing capability and may be formed on a flat substrate or integrated into a flexible substrate. In any event, the microchip 162 is preferably small enough and/or flexible enough so that it can be integrated into protective sleeve 128 without decreasing the resiliency of the protective sleeve and/or may be configured in an annular shape and "wrapped" around the lead. It may be used to identify the lead type and characteristics, as well as other useful data that may be downloaded to the microchip. The communication system is capable of automatically identifying one or more additional IMDs such as the leads that may be associated with the IMD. Additionally, information may be downloaded to the microchip regarding the safe use of diagnostic devices including, among others, a magnetic resonance imagery (MRI) device. IMDs are checked for safe use with such diagnostic devices prior to commercial release of the IMD. The longevity of the IMD, however, as well as the development of newer diagnostic devices in subsequent years, often leaves a physician wondering if the IMD is safe for use with a newer MRI device. Thus, a listing of diagnostic devices deemed safe and compatible for use with the IMD would be of significant value to medical personnel who interact with patient who have an IMD.

In one embodiment, the invention includes a first communication circuit that is attached to, or integrated within, protective sleeve 160. The communication circuit stores data such as model and serial numbers, technical information, and calibration data. At the time of implant or sometime thereafter, information stored by the first communication circuit may be transferred to a second communications circuit that is external to the sleeve. The second communications circuit may reside within the IMD, an external programmer, a personal data management (PDM) unit, or within any other unit such as a Personal Digital Assistant (PDA) that is located within a predetermined range of the first communication circuit. This transferred data can be used both to indicate the presence of the lead, and to identify lead type. Such information can be used, for example, to automatically configure the connector block of the IMD to properly couple to the lead. The data can further be used to automatically adjust amplifier gains or other circuitry associated with the lead. The data may be entered into a patient record on an external programmer, or may be transferred to a central storage location for use by health care providers when performing diagnosis and therapy associated with the IMD. If required by the size of the communications circuitry, or if otherwise desired, the protective sleeve can be any diverse size or shape to accommodate same. That is, the protective sleeve can be of such size and shape as to allow the communication circuitry to be embedded therein. The protective sleeve may be constructed of any resilient, somewhat deformable biocompatible material, such as polyurethane (having a relatively soft durometer value), silicone rubber, and the like.

In another embodiment, the data provided by the first communications circuit includes identification and calibration information concerning additional components of the system. For example, physiologic sensors carried on the leads may be identified so that the IMD can enable and calibrate internal circuitry to receive the physiologic signals. This allows certain functions within the IMD to automatically be enabled only when a component is present in the system so that power can otherwise be conserved. Any other components of an IMD may be identified and calibrated by using a communication circuit according to the current invention. This may include implantable devices such as pluggable antennas, electrodes that can be selectively coupled to the IMD case, and any other types of components that may be added to the system.

According to one aspect of the system, the first communication circuit may be a passively-powered RF transponder. The transponder receives power from an external source. Ultrasonic, optical, and electromagnetic power may be used to power the first communication circuit. In another embodiment, the first communication circuit may receive power from its host unit, such as via the conductors of a lead. According to another aspect of the system, the first communication circuit may include a receiver as well as a transmitter to receive data signals from an external source. This allows the first communication circuit to be programmed with identification, calibration, and other data at the time of component manufacture.

The preceding specific embodiments are illustrative of the practice of the invention. It is to be understood, therefore, that other expedients known to those of skill in the art or disclosed herein may be employed without departing from the invention or the scope of the appended claims. It is therefore to be understood that the invention may be practiced otherwise than is specifically described, without departing from the scope of the present invention. As to every element, it may be replaced by any one of infinite equivalent alternatives, only some of which are disclosed in the specification.

We claim:

1. An improved coupling for an implantable medical device, comprising:

a header module having at least one non-standard port;

a low profile connector having an outer diameter approximately equal to the inner diameter of the port and adapted to frictionally seat within said non-standard port;

a protective sleeve member adapted to couple the low profile connector to the non-standard port;

wherein the non-standard port has an axial passageway coupling opposing sides of the header module and said axial passageway comprises a low profile connector-receiving portion aligned with a pull-tool receiving portion and wherein the low profile connector-receiving portion has a smaller inner diameter than a standard IS-1 port or a standard DF-1 port; and an operable microchip-based communication circuit coupled to the protective sleeve member and wherein the operable microchip-based communication circuit receives operational energy from a remote source of power and said remote source of power is at least a one of the following: an ultrasonic power source, an optical power source, an electromagnetic power source, a power source of an implantable medical device, and a power source coupled to a conductor of a medical electrical lead.

2. The improved coupling of claim 1, wherein the operable microchip circuit further comprises a read/write memory device and a communication circuit for wireless communication with remote equipment.

3. The improved coupling of claim 1, wherein the operable microchip circuit further comprises at least one of the group: an application specific integrated circuit, an integrated circuit, a programmable logic device, an electrically erasable programmable read only memory, a radio frequency receiver, a radio frequency transponder, an interrupt-driven microprocessor, a static random access memory structure, and a dynamic random access memory structure, a flexible circuit substrate.

4. The improved coupling of claim 1, wherein the protective sleeve is a deformable annular sleeve.

5. The improved coupling of claim 4, further comprising a longitudinal gap formed in the annular sleeve.

6. The improved coupling of claim 4, wherein the non-standard port has a first interlocking structure and the annular sleeve has a second interlocking structure which cooperates with the first interlocking structure to form a seal for the non-standard port, and wherein said seal is free of adhesive.

7. The improved coupling of claim 6, wherein said first interlocking structure comprises at least one of the following: an annular ridge, an annular groove, a two sided annular structure defining an apex portion, a cylindrically-shaped strain relief bore opening to the external surface of the header module and having a diameter greater than the low profile connector-receiving portion or a conically-shaped strain relief bore opening to the surface of the header module.

8. The improved coupling of claim 1, further comprising a pull tool having a distal end adapted for insertion through the pull-tool receiving portion of the non-standard port and further adapted to engage a proximal end portion of the low profile connector.

9. The improved coupling of claim 8, wherein the pull tool further comprises an enlarged head portion and the length of said pull tool is greater than the length of the axial passageway.

10. The improved coupling of claim 9, further comprising a mechanical stop surface disposed between the connector-receiving portion and the pull-tool receiving portion.

11. The improved coupling of claim 1, further comprising a pull device at least partially disposed in the axial passageway.

12. An improved coupling for an implantable medical device, comprising:

a header module having either an IS-1 port or a DF-1 port and a non-standard port formed therein and wherein said non-standard port has an enlarged opening, and a reduced diameter opening coupled to the enlarged opening, and wherein at least one electrically conductive pad is disposed on a surface of the enlarged opening;

a low profile connector having a proximal end adapted to fit snugly in a portion of the enlarged opening, wherein said low profile connector has at least one corresponding electrically conductive pad disposed near said proximal end;

an annular protective sleeve member wrapped around a portion of the end region of the low profile connector; and an elongated pull tool having a distal end adapted to be inserted into the reduced diameter opening to thereby engage the proximal end of the low profile connector so that the low profile connector can be manually pulled to establish positive electrical communication between the at least one electrically conductive pad and the at least one corresponding electrically conductive pad, wherein the annular protective sleeve further comprises a microchip-based radio frequency transponder having a memory storage unit and wherein the transponder is adapted to transmit and receive information from a remote radio frequency interrogation device.

13. The improved coupling of claim 12, wherein said memory storage unit stores at least one of the following codes: a lead type code, a date code, a model code, a serial number code, a calibration code, an MRI compatibility code, a technical information code, a client code, a hospital code, a physician code, a patient code, a programming code, an amplifier gain code, a circuitry-update code, a service code or a version code.

14. The improved coupling of claim 12, wherein the perimeter of the enlarged opening has a rounded edge disposed at the junction of the enlarged opening and the exterior surface of the header module.

15. The improved coupling of claim 14, wherein the enlarged opening comprises a outer major opening and a inner minor opening and the at least one conductive pad is disposed in the inner minor opening and the outer major opening is adapted to sealingly receive an interlocking part of the protective sleeve which is coupled to the protective sleeve.

16. A connector assembly for receiving a non-standard low profile medical lead, comprising:

a non-standard lead connector coupled to a low profile medical lead, wherein said non-standard lead connector has a maximum outer diameter less than the outer diameter of a standard IS-1 medical lead and a standard DF-1 medical lead;

a connector module having a non-standard port formed therein, said port having a mechanical stop at a predetermined depth and an axial bore formed through the mechanical stop and emerging on an opposite side of said connector module, wherein said non-standard port has a cylindrical low profile lead engagement region of approximately the same inner diameter as the outer diameter of the non-standard lead connector;

at least one electrically conductive pad disposed in the low profile lead engagement region;

an elongated pull tool disposed at least partially in the axial bore and the non-standard port and wherein a distal end of the elongated pull tool is adapted to mechanically engage the non-standard lead connector;

a resilient annular sleeve adapted to wrap around a portion of the low-profile lead connector and to establish contact with a portion of the non-standard port; and a microchip-based computerized processor coupled to the resilient annular sleeve.

* * * * *